United States Patent [19]

Schroeppel

[11] Patent Number: 4,543,955
[45] Date of Patent: Oct. 1, 1985

[54] SYSTEM FOR CONTROLLING BODY IMPLANTABLE ACTION DEVICE

[75] Inventor: Edward A. Schroeppel, Miramar, Fla.

[73] Assignee: Cordis Corporation, Miami, Fla.

[21] Appl. No.: 519,142

[22] Filed: Aug. 1, 1983

[51] Int. Cl.⁴ .................. A61B 5/00; A61N 1/00; A61M 5/00

[52] U.S. Cl. .................. 128/635; 128/419 PG; 604/66

[58] Field of Search .......... 128/419 PG, 635; 604/65-67

[56] References Cited

U.S. PATENT DOCUMENTS

| | | | |
|---|---|---|---|
| 3,593,718 | 7/1971 | Krasner et al. | 128/419 P |
| 3,777,762 | 12/1973 | Nielsen | 128/419 P |
| 3,830,242 | 8/1974 | Greatbatch | 128/419 P |
| 3,837,339 | 9/1974 | Aisenberg et al. | 604/66 |
| 3,867,950 | 2/1975 | Fischell | 128/419 PG |
| 4,009,721 | 3/1977 | Alcidi | 128/419 PG |
| 4,016,866 | 4/1977 | Lawton | 128/635 |
| 4,055,175 | 10/1977 | Clemens et al. | 604/66 |
| 4,073,292 | 2/1978 | Edelman | 604/66 |
| 4,088,138 | 5/1978 | Diack et al. | 128/419 PG |
| 4,114,628 | 9/1978 | Rizk | 128/419 PG |
| 4,140,132 | 2/1979 | Dahl | 128/419 PG |
| 4,202,339 | 5/1980 | Wirtzfeld et al. | 128/419 PG |
| 4,223,679 | 9/1980 | Schulman et al. | 128/419 PT |
| 4,226,244 | 10/1980 | Coury et al. | 128/419 P |
| 4,228,803 | 10/1980 | Rickards | 128/419 PG |
| 4,236,525 | 12/1980 | Sluetz et al. | 128/419 P |
| 4,313,441 | 2/1982 | Buffet | 128/419 PG |
| 4,316,472 | 2/1982 | Mirowski et al. | 128/419 D |
| 4,333,473 | 6/1982 | Eberhard et al. | 128/635 |
| 4,392,849 | 7/1983 | Petre et al. | 604/66 |
| 4,399,820 | 8/1983 | Wirtzfeld et al. | 128/419 PG |
| 4,428,378 | 1/1984 | Anderson et al. | 128/419 PG |
| 4,436,092 | 3/1984 | Cook et al. | 128/419 PG |
| 4,436,094 | 3/1984 | Cerami | 128/635 |
| 4,441,498 | 4/1984 | Nordling | 128/419 PG |
| 4,467,807 | 8/1984 | Bornzin | 128/419 PG |
| 4,494,950 | 1/1985 | Fischell | 128/903 |

Primary Examiner—William E. Kamm
Assistant Examiner—Mitchell J. Shein
Attorney, Agent, or Firm—Henry W. Collins; Thomas R. Vigil

[57] ABSTRACT

The system includes a sensor assembly comprising a body implantable physiological sensor for controlling a body implantable action device operable to act upon the body in response to changes in a physiological parameter sensed by the sensor. The body implantable action device can be a heart pacing device, a drug infusion pump, or other device which acts upon a human body. The sensor assembly includes a transmitter for transmitting coded signals to the action device which has programming circuitry for deciphering the signals received from the sensor assembly generated by the sensor which is in a location away from the location of the action device. Once these signals have been deciphered, the programming circuitry can adjust the output from the action device, such as the rate and A-V delay of pacing pulses from the pacing circuitry. In one embodiment, the transmitter is a radio transmitter and the programming code transmitted therefrom is picked up by an output terminal, such as a distal electrode of a pacing lead, which acts as a pickup antenna.

26 Claims, 5 Drawing Figures

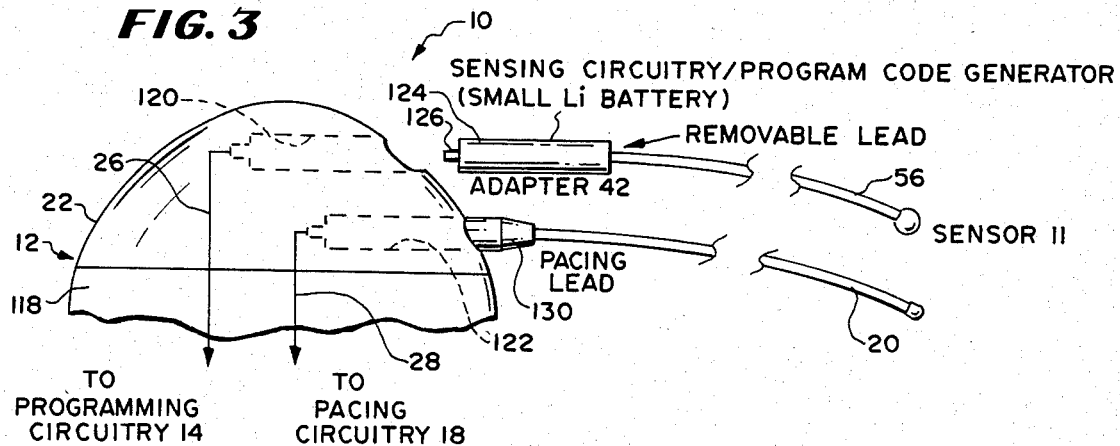
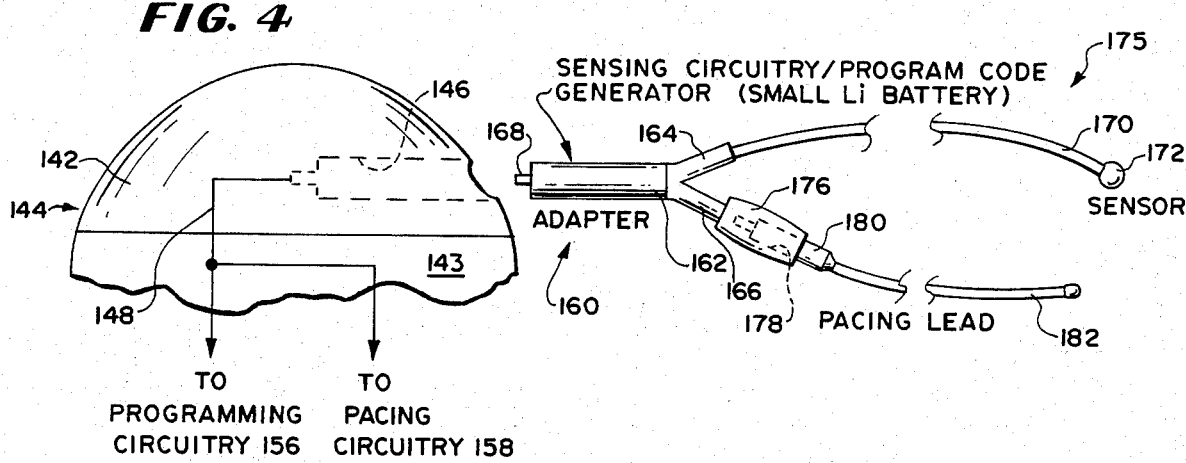
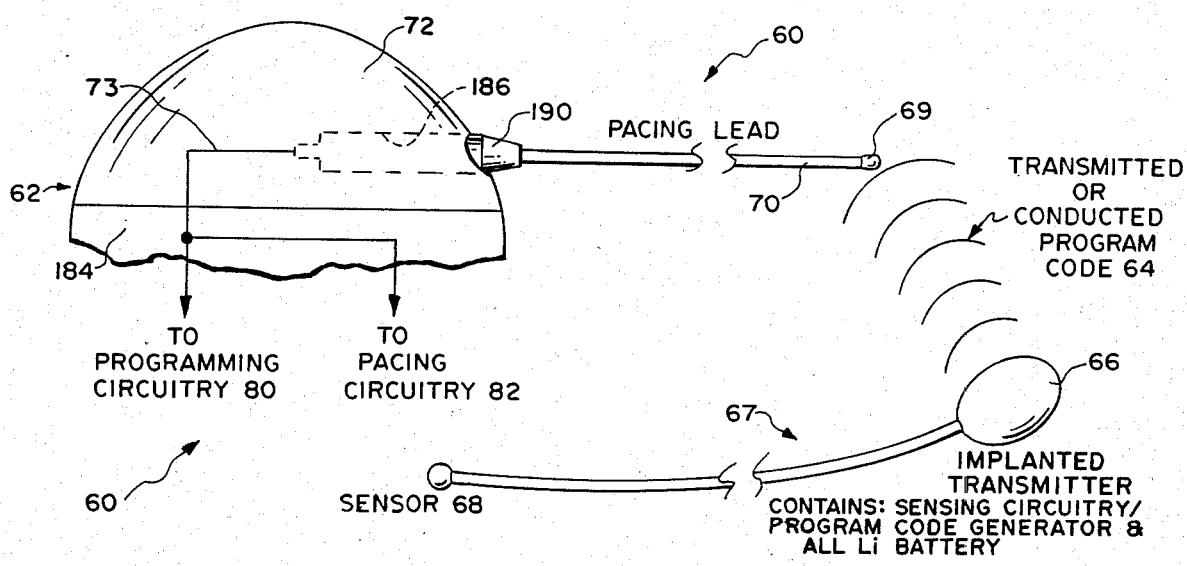

SYSTEM FOR CONTROLLING BODY IMPLANTABLE ACTION DEVICE

BACKGROUND OF THE INVENTION

1. Field of the Invention

The present invention relates to a system for controlling the operation of a body implantable device which is operable to act upon the body in response to changes in a physiological parameter sensed by a physiological sensor. The sensor includes transmission circuitry for transmitting a signal related to the parameter sensed to the device which is operable to decipher the signal and act accordingly upon the body.

2. Description of the Prior Art

Heretofore various implantable devices, such as a pacing device, have been proposed that control parameters that are programmable by using external programming devices, e.g., parameters such as rate of pacing and A-V delay. Also, circuitry has been provided for changing the controlled parameter with programming codes. Example of such previously proposed devices are disclosed in the following patents:

| U.S. PAT. NO. | PATENTEE |
| --- | --- |
| 3,777,762 | Nielsen |
| 3,830,242 | Greatbatch |
| 4,223,679 | Schulman et al. |
| 4,226,244 | Coury et al. |
| 4,228,803 | Richards |
| 4,236,525 | Sluetz et al. |
| 4,313,441 | Buffet |
| 4,316,472 | Mirowski et al. |

The Nielsen U.S. Pat. No. 3,777,762 discloses a pacemaker having an output control circuit which is adapted, when activated, to control pacing pulses in such a manner that the amplitude of each pulse is slightly less than that of the preceding pulse. The control circuit can be activated and deactivated from outside the body, either by suitable hospital equipment, or manually by a surgeon. The control circuit ascertains the smallest pacing pulse that causes heart contraction thereby to permit a threshold value of the heart to be determined without surgical operation.

The Greatbatch U.S. Pat. No. 3,830,242 discloses a remotely operated control system for controlling operation of an electrical pulse generator, such as a cardiac pacer, having timing circuitry for controlling the generation of pulses and signal responsive circuitry for resetting the timing circuitry in response to ventricular electrical signals. The system also includes a portable transmitter operable to selectively generate r.f. signals having different envelope durations. A circuit responsive to the r.f. signals is coupled to the pulse generator and is operable to detect, rectify and filter the r.f. signals and then produce corresponding command signals for causing an increase or decrease in the rate of pulse generation.

The Schulman et al. U.S. Pat. No. 4,233,679 discloses an FM/FM or FM/AM modulated telemetry signal generator for supplying a control signal to a living tissue stimulator implanted in a body. The signal generator includes an externally located oscillator that is controlled by impedance changes in an impedance reflecting circuit located in the implantable tissue stimulator.

The Coury et al. U.S. Pat. No. 4,226,244 discloses a preformed electrical connector for use with a body implantable stimulator, such as heart pacemaker, having a signal generator. The stimulator, e.g., a pacer, has one or two electrical leads electrically and mechanically connected to the pulse generator through one or two preformed electrical connectors mounted in the pacer body containing the signal generator.

The Rickards U.S. Pat. No. 4,228,803 discloses a cardiac pacemaker having means for automatically adjusting the rate of operation to correspond to physiological changes. Circuitry is provided for detecting the presence or absence of an evoked T wave following a delivered stimulus pulse, and for measuring the time interval between the stimulus pulse and the following T wave. The escape interval from the pacemaker pulse generator is varied in accordance with the detected stimulus T interval and in the same direction so as to vary the pacing rate in accordance with variations in such interval. Since this interval in turn corresponds to physiological changes, the pacemaker is adapted to automatically follow the patient's physiological changes. Here signals are sensed from the pacemaker itself without the use of special detectors for sensing conditions elsewhere in the body.

The Sluetz et al. U.S. Pat. No. 4,236,525 discloses an apparatus and method for manually altering the function of distal electrodes of a body implantable tissue stimulator assembly. In one exemplary embodiment, the polarity of the distal electrodes may be reversed by axially repositioning the proximal connectors within the female connector assembly of a tissue stimulator.

The Buffet U.S. Pat. No. 4,313,441 discloses a process for regulating, by means of an extra-corporeal control unit, an implanted cardiac stimulator comprising a pulse generator and a pair of electrodes. The stimulator is controlled so that it functions at a fixed rhythm independent of normal cardiac rhythm. The extra-corporeal unit detects successive pulses emitted by the stimulator. After each of the selected stimulator pulses detected, and during the whole period between successive stimulator pulses, a train of successive control pulses is transmitted by the extra-corporeal control unit and is received by the stimulator. No train of successive control pulses is transmitted during the whole period between other successive stimulator pulses The Mirowski et al. U.S. Pat. No. 4,316,472 discloses an externally controlled implantable electronic device for delivering a cardioverting pulse of energy to the atrium of an ailing heart. In one embodiment, the device is particularly suited for use when the patient visits the office of his physician, and contemplates the transmission of both information and powering energy through the skin of the patient. In another embodiment, the device can be readily operated at home, by the patient, and without the intervention of the physician. Here the source of energy is permanently implanted.

As will be described in greater detail hereinafter, the system for controlling a body implantable action device of the present invention differs from the systems previously proposed by providing a remote sensor that is capable of sensing physiological parameters, that is coupled directly or indirectly to the body implantable device, and that generates programming codes for controlling the operating parameters of the body implantable device such as a pacemaker. In one embodiment of the present invention, the remote sensor is electrically coupled to a transmitter which sends electrical signals, which can be radio frequency signals, to the action device such as a pacemaker, and wherein a distal electrode of a pacing lead acts as an antenna to pick up and transmit the radio signals to the pacemaker.

SUMMARY OF THE INVENTION

According to the invention there is provided a system for controlling operation of a body implantable action device which is operable to act upon the body in response to changes in a parameter sensed, said system including a sensor assembly which is separated from the action device, which is capable of being implanted within a body and which includes a sensor for sensing a physiological parameter in a body, signal converting circuitry, such as a program code generator, for converting signals, such as conventional digital program codes of the type normally used in the action device, and transmitting means for transmitting said coded electrical signal related to the parameter sensed to the action device which is operable to decipher the coded electrical signal and act accordingly upon the body.

BRIEF DESCRIPTION OF THE DRAWINGS

FIG. 3 is a fragmentary elevational view of one embodiment of a pacing device of the present invention which has two sockets for receiving and electrically coupling to a pacing lead terminal electrode and to an adapter connected to a sensor and forming therewith one embodiment of the sensor assembly of the present invention.

FIG. 4 is a fragmentary elevational view of another embodiment of a pacing device of the present invention which has one socket for receiving and electrically coupling to a Y-shaped adapter having an electrode assembly which is received in the pacing device socket, a leg connected directly to a sensor and a leg with a socket for coupling to the terminal electrode of a pacing lead assembly.

FIG. 5 is a fragmentary elevational view of another embodiment of a pacing device of the present invention which has one socket for receiving and electrically coupling to a terminal electrode of a pacing lead assembly which is capable of receiving signals from a remote transmitter in a sensor assembly of the present invention.

DESCRIPTION OF THE PREFERRED EMBODIMENTS

Figure 1:
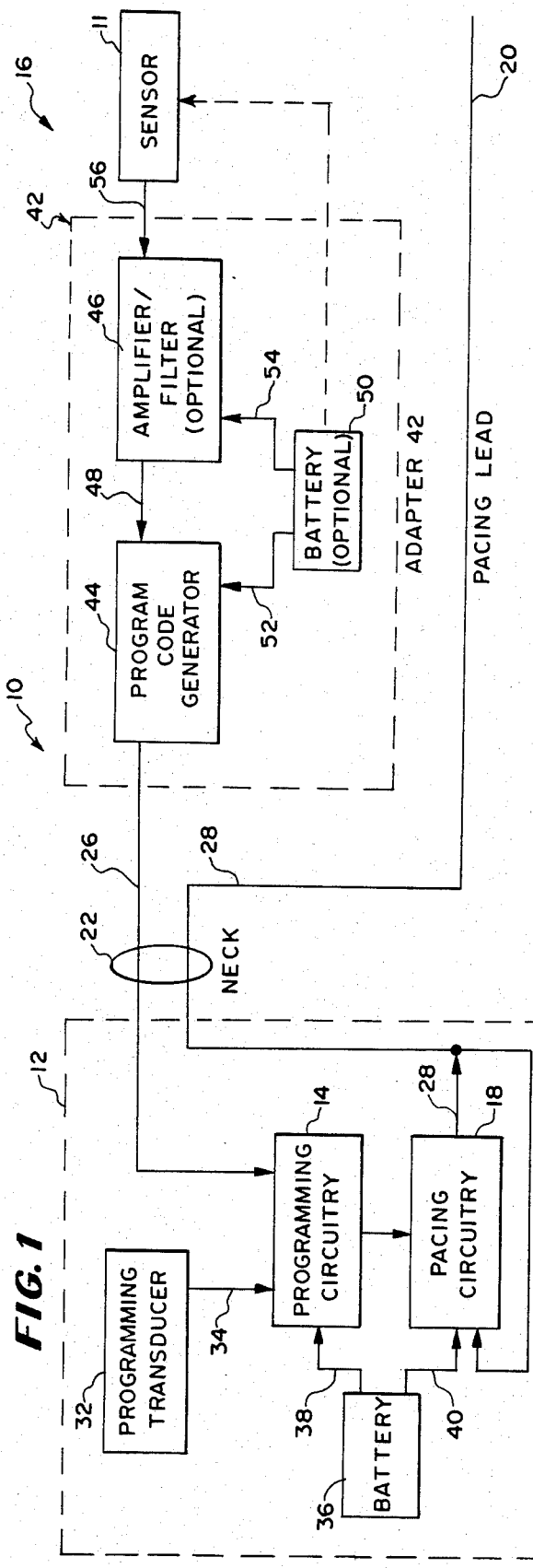
FIG. 1 is a block schematic diagram of one embodiment of the system for controlling a body implantable action device of the present invention and shows a body implantable pacing device electrically coupled to a sensor assembly of the system and to a pacing lead assembly.

Referring now to the drawings in greater detail, there is illustrated in FIG. 1 a block schematic circuit diagram of one embodiment of a system 10 constructed in accordance with the teachings of the present invention for coupling a remote sensor 11 to an action device 12 such as an implantable pacer 12, or drug infusion pump. The action device 12 can be any type of action device which acts upon a human body and the one illustrated here is an implantable pacer 12.

As shown, the action device 12 includes programming circuitry 14 which is operable to decipher signals received from a physiological sensor assembly 16 which includes the sensors 11 implanted in a human body in a location away from the device 12. The programming circuitry 14 adjusts the operating parameters of pacing circuitry 18 in the device 12 in response to the signals deciphered which in turn are generated from body parameters sensed by sensor 11. The pacing circuitry 18 then supplies adjusted electrical pulses to a pacing lead assembly 20 which acts upon the heart.

The device 12 further includes a neck 22 through which the sensing assembly 16 and pacing lead assembly 20 are coupled to the pacing circuitry 18. This connection is represented by conductors 26 and 28.

The action device 12 further includes a programming transducer 32 which is electrically coupled to the programming circuitry 14 by a conductor 34, and a power supply 36, preferably a lithium battery 36, which is electrically coupled to the programming circuitry 14 and the pacing circuitry 18 by conductors 38 and 40 respectively.

The neck 22 of the action device 12 has two electrical receptacles or sockets (such as sockets 120 and 122 shown in FIG. 3) where conductors 26 and 28 are coupled with the sensor assembly 12 and the pacing lead 20. More specifically, the conductor 26 is coupled to an adapter 42 of the sensor assembly 16. The adapter 42 includes a program code generator 44 having an output coupled to conductor 26 and an input coupled by a conductor 48 to an amplifier and filter 46. If desired, a power supply 50, such as a lithium battery, can be mounted in the adapter 42 and coupled to the program code generator 44 and amplifier and filter 46 by conductors 52 and 54 respectively. Alternatively, the sensor data transmitting circuitry in the adapter 42 can be powered by the battery 36 in the pacer 12.

The amplifier and filter 46 receives electrical signals from the physiological sensor 16 generated by the sensing of physiological parameters by physiological sensor 16 through a sensor lead 56, and amplifies and filters the signals if necessary. The parameters sensed can be, for example, body temperature, blood oxygen concentration or blood potassium concentration.

The conditioned signals can then be supplied to the program code generator 44. The program code generator 44 then generates a desired digital programming code which is supplied through the neck 22 of the device 12 to the programming circuitry 14. The programming circuitry 14 then determines whether parameters of the pacing signals, such as the rate and A-V delay, should be adjusted in light of the parameters sensed. The adjusted pacing signals are then supplied to pacing lead 20.

By manufacturing an action device 12 as described above having circuitry capable of recognizing certain programming codes, such device 12 can be interfaced on implantation thereof, or be interfaced later, with an appropriate sensor assembly including an appropriate sensor 11 and sensor data transmitting circuitry 44, 46, 50 in an adapter 42. This arrangement permits less expensive testing and modification of the particular sensor 11 and transmitter/adapter 42 utilized, as well as allowing sensors 11 to be interfaced with devices 12 that have already been implanted. In this respect, the programming code from the sensor assembly 16 is easily introduced into the action device 12 through the neck 22 thereof.

Figure 2:
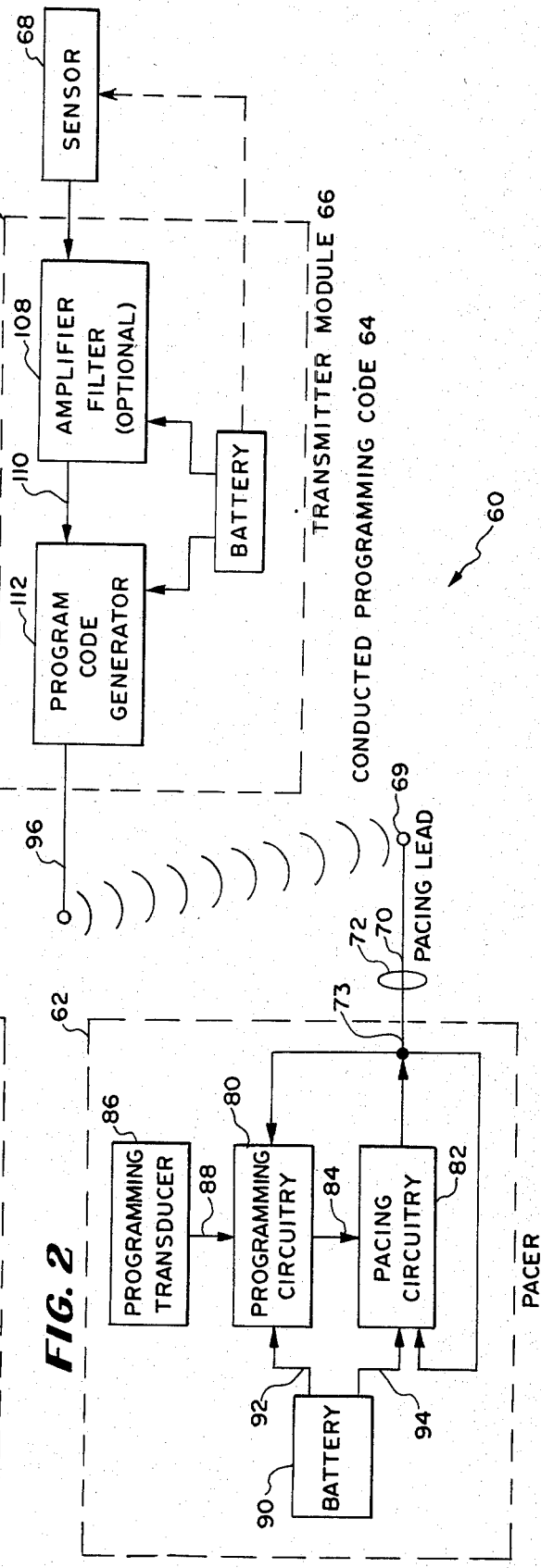
FIG. 2 is a block schematic diagram of another embodiment of the system of the present invention and shows a sensor assembly including a transmitter for transmitting signals to a distal electrode of a pacing lead assembly coupled to a body implantable pacing device.

Referring now to FIG. 2, there is shown therein a block schematic circuit diagram of another embodiment of a system 60 constructed according to the teachings of the present invention. The system 60 includes an action device 62 which receives programming codes 64 conducted through body tissue that are transmitted from transmitter module 66, forming part of a sensor assembly 67 with a sensor 68, to a distal electrode 69 of a pacing lead 70 which acts as a pickup electrode or antenna. The system 60 constructed in this manner provides great flexibility in the positioning of the action device 62, the transmitter module 66 and the sensor 68 because of the absence of electrical conductors between the transmitting module and the action device 62 and this is particularly advantageous in certain applications, such as where the action device 62 is a drug infusion device. This arrangement also provides for easy access to the transmitter module if it is positioned just within or on the outside of a human body. Thus, a physician may be able to make minor adjustments, or replace a battery, without taking unnecessary invasive measures.

The transmitting module 66 can be constructed to transmit electrical signals or radio frequency signals.

The action device 62 has electrical circuitry therein including one electrical receptacle or socket (such as the socket 186 shown in FIG. 5) in a neck 72 of the device 62 for receiving and electrically coupling the lead 70 to a conductor 73. The circuitry also includes programming circuitry 80 and pacing circuitry 82 which are interconnected by conductor 84. A programming transducer 86 is connected to programming circuitry 80 by a conductor 88 and a battery 90 is electrically connected to the programming circuitry 80 and the pacing circuitry 82 by conductors 92 and 94 respectively. As shown, the conductor 73 is connected to an input of the programming circuitry 80 and to an input and to an output of the pacing circuitry 82. Signals from an output 96 of the transmitting module 66 are picked up by electrode 69 and supplied via the pacing lead 70 and the conductor 73 to the programming circuitry 80 where such signals are deciphered. Once the conducted program code 64 is deciphered, the deciphered code is used to adjust, if required, the operating parameters, e.g., rate and A-V delay, of the pulses supplied to the pacing lead 70 which is plugged into the socket in the neck 72.

The transmitter module 66 includes an amplifier and filter 108 coupled to physiological sensor 68 whereby the electrical signals from the sensor can be filtered and amplified, if necessary. The conditioned electrical signals are then supplied via a conductor 110 to a program code generator 112 where the proper digital program code 64 is generated and supplied to output 96 for transmission through body tissue to distal electrode 69. The transmitter module 66 is powered by a lithium battery 111.

According to the teachings of the present invention, once the electrical parameters of pacing pulses generated by the systems 10 or 60 are properly adjusted relative to the physiological parameters sensed, they are supplied to pacing leads 20 or 70 through neck 22 or 72 of the device 12 or 62 to act accordingly on a body. It is noted that electrical parameters, e.g., rate and A-V delay, of pulses from pacing devices disclosed in the prior art are presently programmable through external programming devices By providing device 12 or 62 with the circuitry required to recognize program codes based on physiological parameters sensed according to the teachings of the present invention, such device can be later interfaced with appropriate sensors and appropriate signal transmitters. In this way, as refinements are made in sensors and transmitters, devices 12 or 62 permit a new sensor and transmitter to be implanted in a body and interfaced with a device 12 or 62 already implanted.

Referring now to FIG. 3 there is shown therein the pacer device 12 with the neck 22 in a body 118 of the device 12. The neck 22 has two electrical receptacles or sockets 120 and 122 which are electrically coupled to the programming circuitry 14 and the pacing circuitry 18 by conductors 26 and 28 respectively. The transmitter/adapter 42 plugs into electrical receptacle 120 and has a terminal pin 126 which makes electrical contact with conductor 26. A removable sensing lead 56 is attached to the adapter 42 and has the physiological sensor 11 mounted at its distal end.

Once the program code is received and deciphered by the internal circuitry of the device 12, adjusted (if necessary) pacing pulses are supplied from pacing circuitry 18 through conductor 28 to the electrical receptacle 122 in which is received a terminal electrode assembly 130 of the pacing lead 20 to supply the adjusted pacing pulses to the pacing lead 20.

The structure shown in FIG. 3 allows for the future implementation of adapters 42 that may have transmitters which are designed and fabricated more easily without requiring alterations to the electronics of the device 12. Furthermore, the efficacy of various sensors can be tested without requiring changes to the electronics of the device 12. Devices 12 manufactured with a neck 22 constructed in accordance with the teachings of the present invention can receive two adapters 42 and 130 with the adapter 42 being chosen from one of several adapters having the same shape but different electronics therein.

Referring now to FIG. 4 there is shown therein another embodiment of the system of the present invention wherein a neck 142 in a body 143 of an action device 144 has one electrical receptacle or socket 146 electrically connected to a conductor 148 which is coupled to the programming circuitry 156 and pacing circuitry 158 respectively. A specially designed Y-shaped adapter 160 has a main body portion 162 received in the socket 146 and has two legs 164 and 166 extending therefrom.

The circuitry of a transmitter is contained in the body portion 162 of adapter 160 and such circuitry has an output at terminal pin 168 which makes contact with conductor 148 in socket 146. The leg 164 is electrically coupled via a sensing lead 170 to a physiological sensor 172 and together adapter 160, lead 170 and sensor 172 form a sensor assembly 175. Leg 166 has an adapter 176 with a socket 178 for receiving a terminal electrode assembly 180 of a pacing lead assembly 182. In this embodiment of the system 160, the circuit connection in the pacer body 143 is substantially the same as shown in pacer 62 in FIG. 2. Also the circuitry in adapter body portion 162 is substantially as shown in adapter 42 in FIG. 1 with or without a battery 50.

Referring now to FIG. 5, there is shown therein a structural realization of the system 60 shown in FIG. 2. Here the action device or pacer 62 has a body 184 having one electrical receptacle or socket 186 for receiving a terminal electrode assembly 190 of pacing lead 70.

By providing the device 62 with neck 72 constructed in accordance with the teachings of the present invention either a Y-shaped adapter 160 can be utilized as shown in FIG. 4 or a pacing lead 70 and a sensor assembly 67 with a transmitter module 66 can be utilized as shown in FIG. 5.

In the latter system (as shown in FIGS. 2 and 5), the program code can be conducted by body tissue or a radio frequency type transmitter can be used.

The programming codes are preferably generated and transmitted at frequencies distinguishable from the body potentials that are picked up by the distal electrode of the pacing lead assembly.

Also the action device 12, 62 or 144 can be an infusion device such as a drug infusion device or an insulin infusion device such as of the type disclosed in U.S. Pat. Nos. 4,248,711 and 4,265,241.

From the foregoing description it will be apparent that the systems 10 and 60 of the present invention have a number of advantages, some of which have been described above and others of which are inherent in the invention. Also it will be apparent that modifications can be made to the systems 10 and 60 without departing from the teachings of the present invention. Accordingly, the scope of the invention is only to be limited as necessitated by the accompanying claims.

I claim:

1. In a system comprising a body implantable device and a sensor assembly for programming or reprogramming said action device, which device is operable to act upon the body in response to changes in a sensed parameter and which has circuitry for deciphering coded signals used to program said device, the improvement comprising said sensor assembly being a separate, independent assembly which is independent of the action device, which is capable of being implanted within a body, and which includes:

sensor means for sensing a physiological parameter in a body, signal converting circuitry means for converting signals generated by said sensor means to coded electrical signals, such as conventional digital program codes of the type normally used in programming or reprogramming the action device, and transmitting means for transmitting said coded electrical signal related to the sensed parameter to the action device which is operable to decipher the coded electrical signal and act accordingly, upon the body.

2. The system of claim 1 wherein said action device circuitry includes pacer programming circuitry, a program transducer, pacing circuitry and a self-contained power supply coupled together.

3. The system of claim 1 wherein said action device is a body implantable medical dispensing device.

4. The system of claim 3 wherein said action device includes means for adjusting the metering dosage of the medical dispensing device relative to the physiological parameter sensed.

5. The system of claim 1 wherein said action device is a body implantable pacemaker.

6. The system of claim 5 wherein said action device includes a body having first and second socket means therein, one for receiving an adapter of said sensor assembly and one for receiving a terminal electrode assembly of a pacing lead.

7. The system of claim 5 wherein said action device includes means for adjusting the parameter of a pacing pulse (e.g. rate and/or A-V delay) relative to the physiological parameter sensed.

8. The system of claim 5 wherein, said sensor assembly includes an adapter and said action device includes a body portion having socket means therein for receiving a terminal electrode assembly of a pacing lead or said adapter of said sensor assembly.

9. The system of claim 8 wherein said socket means receives a terminal electrode assembly of a pacing lead which also has a distal electrode assembly with at least one electrode capable of acting as a pick-up electrode for picking up signals generated by said transmitting means.

10. The system of claim 9 wherein said transmitting means includes a radio frequency transmitter.

11. The system of claim 8 wherein said adapter is a Y-shaped adapter having a body portion and two legs.

12. The system of claim 1 wherein said body portion has said transmitting means mounted therein.

13. The system of claim 11 wherein one of said legs is coupled to a lead connected to said sensor.

14. The system of claim 11 wherein one of said legs includes a socket for receiving a terminal electrode assembly of a pacing lead.

15. The system of claim 1 wherein said sensor includes means for sensing physiological parameters and is capable of being placed in the body at a location away from the location where said action device acts upon the body.

16. The system of claim 1 wherein said transmitting means comprise an electrical conductor.

17. The system of claim 1 wherein said transmitting means is defined by the bulk conductivity through body tissue.

18. The system of claim 1 wherein said transmitting means comprise a radio frequency transmitter.

19. The system of claim 1 wherein said transmitting means is mounted in an adapter which can be plugged into a socket in the action device.

20. The system of claim 19 wherein said sensor assembly includes a lead coupled to and between said adapter and said sensor.

21. The system of claim 1 wherein said transmitting means includes means for filtering and amplifying signals received from said sensor.

22. The system of claim 1 wherein said signal converting circuitry includes a self-contained power supply.

23. The system of claim 22 wherein said power supply is a lithium battery.

24. The system of claim 1 wherein said sensor includes means for sensing blood oxygen concentration.

25. The system of claim 1 wherein said sensor includes means for sensing blood potassium concentration.

26. The system of claim 1 wherein said sensor includes means for sensing body temperature.

* * * * *